United States Patent [19]

Baierl

[11] 4,016,180

[45] Apr. 5, 1977

[54] CHEMICAL CONCENTRATION BY ADSORPTION

[75] Inventor: Kenneth W. Baierl, Appleton, Wis.

[73] Assignee: Flambeau Paper Company, Park Falls, Wis.

[22] Filed: June 18, 1975

[21] Appl. No.: 587,849

[52] U.S. Cl. .............................. 260/347.9; 260/428; 260/499; 260/541; 260/598; 260/627 R; 260/643 G; 260/674 A; 162/16; 210/26; 423/659

[51] Int. Cl.$^2$ ................ C07D 307/49; B01D 15/06; B01D 15/08; C07C 53/08

[58] Field of Search ............... 260/347.9, 499, 541, 260/708, 488 F; 162/16; 210/26; 423/659

[56] References Cited

UNITED STATES PATENTS

| 1,960,812 | 5/1934 | Groth et al. | 260/347.9 |
| 2,422,504 | 6/1947 | Spence | 260/708 X |
| 2,779,770 | 1/1957 | Cass | 260/708 X |

FOREIGN PATENTS OR APPLICATIONS

| 332,983 | 8/1930 | United Kingdom | 260/708 |

OTHER PUBLICATIONS

Lynam et al., The Industrial Chemist, p. 109, Mar. 1950.
Mantell, Adsorption, New York, McGraw-Hill, p. 243.

*Primary Examiner*—Henry R. Jiles
*Assistant Examiner*—Bernard Dentz
*Attorney, Agent, or Firm*—Schmidt, Johnson, Hovey & Williams

[57] ABSTRACT

A low cost, two-stage adsorption-desorption method of concentrating dilute supplies of chemicals is provided which uses a minimum of energy in the form of process steam and yields highly concentrated supplies of end products which are suitable for reuse or sale. The methods hereof are particularly adapted for concentrating waste condensates derived from pulp-making operations such as the Kraft or sulfite processes, but in general is also applicable for treating all types of dilute organic or inorganic adsorbable chemicals. The invention involves first adsorbing a chemical fraction from a dilute stream thereof onto activated carbon, followed by regenerating the adsorbed chemicals and concentrating the same by fractional distillation, whereupon the partially concentrated chemicals are again adsorbed, regenerated, subjected to a second fractional distillation concentration step, and recovered. In preferred alternate procedures, aqueous sulfite waste condensates containing minor amounts of acetic acid, methanol, furfural and sulfur dioxide are treated by the methods hereof to yield concentrated quantities of acetic acid, ethyl acetate or furfural.

32 Claims, 6 Drawing Figures

CHEMICAL CONCENTRATION BY ADSORPTION

This invention is concerned with an efficient and economical process for concentrating very dilute streams of chemicals to produce concentrated supplies thereof, or of conversion products derived from such chemicals. More particularly, it is concerned with a dual adsorption-desorption concentration method which is characterized by extremely low stream consumption and simplified operational procedures notwithstanding the fact that very concentrated supplies of end products can be obtained which are suitable for reuse or sale. Although in its particular aspects the invention is concerned with treatment of pulp-making waste condensates, it is to be understood that the methods hereof have wide application, for example, in the purification and decolorization of sugars, alcohols, aldehydes, acids, condensates, dye production effluents and other waste steams. Other organic chemicals amenable to treatment in accordance with the invention include aldehydes, phenols, cymenes, saturated oils, high molecular weight organic impurities, dyes, and taste and odor chemical components.

Paper mills and other chemical processing plants have for a very long time engaged in the practice of simply dumping their process waste effluent streams into the nearest river or stream. This not only presents a real threat to the ecology, but in many instances the discarded materials would have substantial commercial value if they could be concentrated and treated for resale and reuse at a practical cost. In the latter connection, increasing fuel prices and the attendant costs of processing steam and other forms of heat have in many cases made conventional recovery techniques extremely uneconomical and therefore impractical. In view of these factors, workers in the art of chemical recovery techniques have been searching for ways to simply and economically concentrate and recover minor fractions of valuable chemical constituents in production plant effluent streams which have heretofore been discarded.

In the papermaking industry, sulfite pulp-making condensates contain minor proportions of potentially valuable chemicals such as acetic acid, methanol, furfural and sulfur dioxide. These waste streams are extremely dilute, i.e, in many cases are 99% or more water, and this fact of course materially increases the difficulty of extracting these chemical constituents at a practical cost. For example, although it would theoretically be possible to fractionally distill these waste streams to separate out the acetic acid and furfural components for example, as a practical matter the steam consumption attendant to such a distillation procedure would drive the energy expenditure and chemical recovery costs for beyond their commercial value. Thus, there has heretofore been no really successful answer to the problem of concentrating and recovering valuable chemical constituents from extremely dilute streams thereof at a relatively low cost in terms of equipment needs and energy consumption.

It is therefore the most important object of the present invention to provide a simplified, low-cost method of treating dilute steams containing valuable adsorbable chemical fractions in a manner to produce concentrated supplies of such chemicals or of conversion products derived therefrom, notwithstanding minimization of the use of process stream or other forms of energy in the method and the employment of relatively simple equipment and procedures.

Another object of the present invention is to provide a dual absorption-desorption concentration process wherein dilute streams of chemicals, e.g., waste condensates derived from the Kraft or sulfite pulp-making processes, are first treated in a primary concentration stage by adsorption thereof onto activated carbon, followed by regeneration of the carbon by contacting the same with a regeneration agent to replace the initially adsorbed chemicals and produce a supply of primary stage end products, followed by fractionally distilling the desorbed end products in order to at least partially concentrate and/or chemically convert the same, whereupon the partially concentrated chemicals are subjected to another activated carbon adsorption-regeneration step followed by another fractional distillation and recovery of a supply of concentrated end products.

As a corollary to the foregoing, another important object of the present invention is to provide a method wherein aqueous waste condensates from pulp-making procedures which contain minor quantities of acetic acid and furfural can be selectively treated to provide concentrated supplies of acetic acid, ethyl acetate or furfural without drastically altering the treatment apparatus or process techniques.

In it's broadest aspects, the present invention pertains to a two-stage adsorption-desorption concentration process which is operable to concentrate dilute supplies of a wide variety of chemicals to yield concentrated supplies of such chemicals or of conversion products derived therefrom.

The process includes first directing the dilute supply of chemicals (e.g., chemical, petrochemical, textile, Kraft or sulfite process condensates which may be derived from condensed relief, exhaust and/or blow gases and from the evaporation of spent liquors) to a primary concentration zone which contains a first adsorption media, preferably activated carbon. The desired chemicals contained in the dilute supply thereof are then adsorbed onto the first media whereupon the clarified feed can be disposed of or reused.

At this point the adsorbed chemicals are desorbed by contacting the first adsorption media with a first regenerating agent in order to yield a supply of primary stage desorbed products more concentrated than the dilute supply. In the case of treating sulfite waste liquors, this first agent is selected from the group consisting of the lower alcohols, acetone and moisture, or most preferably methanol, ethanol and steam. For example, if the primary stage adsorption column is sized and adapted for adsorbing the acetic acid component of sulfite condensates, regeneration with methanol will initially produce quantities of methyl acetate, while steam regeneration will yield supplies of unconverted acetic acid.

In certain forms of the invention, the next step involves concentrating the desorbed products to yield a supply of primary stage end products which are more concentrated than the initial dilute supply of chemicals. In preferred forms this concentration is effected by fractionally distilling the end products in a conventional two-stage steam-fed fractionator. However, in continuous operations using a solvent more volatile than water (such as methanol), the fractionation step does not serve to concentrate the desorbed supply of chemicals.

The second stage operation of the present method includes the step of directing the primary stage end products to a secondary concentration zone containing adsorption media (again preferably comprising a column packed with activated carbon) whereupon the first stage end products are adsorbed. Desorption of the latter then follows by contacting the second adsorption media with a second regenerating agent (which are preferably the same as in the case of the first regenerating agent) to yield a supply of second stage desorbed products. Finally, the latter products are concentrated, preferably by fractional distillation, and recovered as secondary stage end products.

Although the above two-stage process has been described in terms of separate steps, it is to be understood that the method hereof preferably is conducted on a continuous basis, thus necessitating provision of separate equipment for the primary and secondary stage. Continuous operation also implies provision of recycle lines and holding tanks to be used in conjunction with the adsorption and fractionation columns of each stage in order to most efficiently provide for continuous, uninterrupted running. Of course, such expedients are well known in the art and need not be described in detail herein. Moreover, in cases where a regenerating agent other than steam is employed (e.g., methanol or ethanol), the activated carbon of the respective stages is purged after the desorption step in order to prepare the carbon for further adsorption of chemicals thereon. This purging is preferably carried out by passing steam through the carbon to clear the alcoholic or other regenerating agents therefrom.

The following discussion involves a description of the apparatus and operation of each of the embodiments depicted in the drawings, along with an example demonstrating the use thereof in producing concentrated supplies of valuable chemicals from dilute pulp-making condensates. It is to be clearly understood however, that the following discussion and examples are merely illustrative of the invention but in no way constitute limitations thereon.

Figure 1:
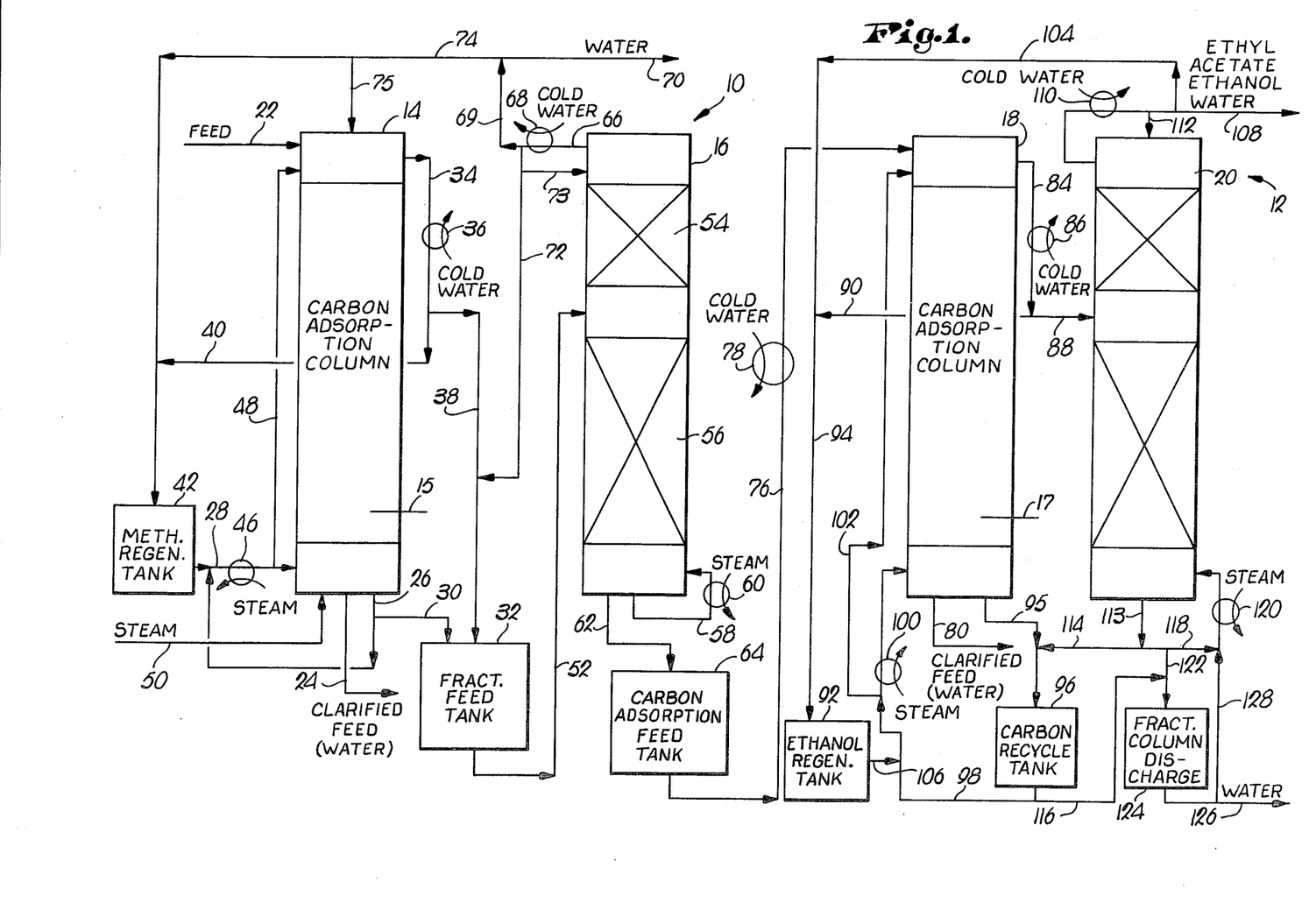
FIG. 1 is a schematic representation of apparatus in accordance with the invention adapted for the production of concentrated supplies of ethyl acetate from a dilute supply of sulfite pulp-making condensates.

FIG. 1 EMBODIMENT

This embodiment of the present invention is particularly adapted for the recovery of ethyl acetate from sulfite pulp-making waste condensates which conventionally contain fractions of methanol, acetic acid, furfural, sulfur dioxide and water. Broadly, the apparatus of FIG. 1 comprises a primary adsorption and concentration stage 10 coupled with a secondary stage 12 operable to produce concentrated ethyl acetate. Primary stage 10 includes the carbon adsorption column 14 and a fractionating column 16, while secondary stage 12 likewise includes an activated carbon filled column 18 and a fractionating column 20.

In more detail, activated carbon column 14 is of conventional variety and is filled with activated carbon which is operable to adsorb at least a portion of the sulfite waste liquor passed therethrough. A temperature sensitive probe 15 is provided adjacent the bottom of column 14 for monitoring operations therein. A feed line 22 is provided at the top of column 14 for the introduction of waste condensates, with an exit line 24 at the bottom of the column for conveying clarified feed. Of course, these lines could readily be reversed, resulting in bottom feed and top outlet. In addition, an outlet line 26 is connected to the bottom of column 14 to provide a recycle which is connected to methanol regeneration line 28 later to the discussed in detail. A product tap-off 30 from line 26 is connected to fractionation column feed tank 32. An upper product line 34 is connected to the top of column 14 and extends through heat exchanger 36. A line 38 is interconnected between line 34 and feed tank 32, with a recycle line 40 interconnecting line 34 and methanol regeneration tank 42. Regeneration line 28 extends between tank 42 and the bottom of tower 14, and passes through a steam-fired reboiler 46. A line 48 is connected to line 28 between reboiler 46 and column 14 and extends to the top of the latter as shown. Finally, a steam line 50 is provided for conveying steam to the bottom of column 14 during purging operations.

A fractionation column feed line 52 is connected to the bottom of tank 32 and connects with column 16 between packing sections 54 and 56 thereof. A recycle line 58 is connected to the bottom of tower 16 and passes through steamfired reboiler 60 as depicted. Furthermore, a recovery line 62 extends between the bottom of tower 16 and collection tank 64. A line 66 extends from the top of tower 16 and passes through heat exchanger 68, with a leg 69 if line 66 interconnecting with water line 70. A return line 72 is interconnected between line 66 on the output side of exchanger 68 and line 38 for return to tank 32, with a loop recycle line 73 being provided between line 72 and column 16. Finally, a leg 74 of line 70 is connected for return to regeneration tank 42, with methanol recycle line 40 being connected to leg 74 as illustrated. In addition, a tap-off line 75 is interconnected between leg 74 and the top of column 14 ar illustrated.

A feed line 76 extends from collection tank 64 to the top of second carbon adsorption column 18 with a heat exchanger 78 being interposed in line 76. A clarified feed line 80 is connected to the bottom of column 18 for the purpose of conveying clarified feed for disposal or reuse. As in the case of column 14, these lines also could be reversed. A product recovery line 84 is connected to the top of column 18 and passes through a heat exchanger 86 and is ultimately connected to fractionation column feed line 88. A recycle line 90 is likewise connected to line 84 for return to ethanol regeneration tank 92 via line 94. A product line 95 is connected to the bottom of the column 18 and extends to collection tank 96 as illustrated. A recycle line 98 is interconnected between the bottom of tank 96 and the bottom of column 18, with a reboiler 100 being interposed within the line. A bypass 102 is connected to line 98 on the source side of reboiler 100 and is connected to the top of tower 18. A short connection line 106 extends between tank 92 and line 98 as shown.

A product recovery line 108 is connected to the top of two-stage fractionation column 20 and passes through a cold water heat exchanger 110. A recycle line 104 is connected at one end thereof to line 108 and ultimately to line 94 leading to ethanol regeneration tank 92. A short line 112 connects product recovery line 108 back to the top of column 20 for providing a loop recycle.

A bottom line 113 is connected to the lower end of column 20 and is attached to a feed leg 114. A line 116 is connected to collection tank 96 and is also operatively attached to a discharge line 122 leading from the fractionation column 20. In addition, a recycle leg 118 is connected to bottom line 113 and extends through reboiler 120 and is ultimately connected to the bottom of column 20. Line 122 is connected to recycle line 118 and feeds into a discharge tank 124. A water line 126 extends from the bottom of tank 124 and has a recycle line 128 extending therefrom which interconnects with line 118 prior to passage through reboiler 120.

The operation of the apparatus depicted to FIG. 1 will now be described in connection with the treatment of waste condensates from a conventional sulfite pulp-making process in order to produce concentrated ethyl acetate. The condensate feed is directed through line 22 to the top of column 14 and allowed to descend through the activated carbon for adsorption thereon. In this connection, such sulfite condensate liquor would normally contain methanol, furfural, acetic acid and water and be quite dilute, for example containing greater than 99% by weight water. During passage of this dilute stream through column 14, the sulfur dioxide (if not previously removed), acetic acid, and furfural fractions would adsorb on the activated carbon with a clarified feed consisting of water and a minor proportion of methanol exiting through line 24. In one commercial embodiment of the present invention, column 14 is sized so that acetic acid begins to break through after about 12 hours of adsorption, at which point the feed stream is diverted to another parallel tower.

After adsorption, methanol from tank 42 is vaporized in reboiler 46 and diverted through line 48 to the top of column 14, whereupon the vaporized methanol descends through the column. This is continued until the methanol level reaches an appropriate point near the bottom of column 14 as measured by a temperature probe 15. This methanol level can be detected by a temperature of approximately 148° F. at probe 15. During such downward travel of the vaporized methanol, methyl acetate (which is the most volatile component) along with a portion of the vaporized methanol are condensed within column 14 and ultimately pass through lines 26, 30 to tank 32. In addition, condensed methanol, water and acetic acid also pass through these lines to tank 32.

After the downward flow of vaporized methanol is discontinued, additional vaporized methanol is directed to the bottom of column 14 through line 28 and is allowed to pass upwardly therethrough in order to give a refluxing action within column 14 which assures greater product separation and recovery. During such travel additional vaporized methyl acetate and methanol pass through line 34, condenser 36 and ultimately to tank 32, while condensed methanol, water and acetic acid travel through lines 26, 30 to tank 32. The effluent leaving line 34 at the top of column 14 is initially a temperature of about 128° F. which signifies that the mixture is primarily methyl acetate. During the regeneration treatment with vaporized methanol however, this temperature gradually rises until it reaches a level of about 148° F. at which point substantially all of the adsorbed acetic acid has been removed from column 14.

The aqueous methanol-methyl acetate mixture within tank 32 passes via line 52 to reflux column 16 which is indirectly steam-fed by provision of reboiler 60 and steam cycle loop line 58. The mixture from feed line 52 is refluxed within column 16 in order to separate out the acetic acid fraction and cause reconversion of the methyl acetate to methanol and acetic acid. This methanol is then returned to tank 42 for reuse. In particular, the initial product leaving column 16 through line 66 is at a temperature of approximately 128° F., again signifying the presence of methyl acetate. During continued refluxing however, the level of vaporized methanol rises within tower 16 as evidenced by a gradual rise in temperature of the mixture leaving tower 16 to a level of approximately 148° F. In any event, during such reflexing before the final temperature is reached, a portion of the mixture is recycled through lines 66, 72 and 73 while another portion is fed via line 69 to leg 74 and line 75 for recycling through the system, while a methanol fraction from line 34 is returned to tank 42 through lines 40, 74. In addition, an appropriate portion of the product mixture leaving column 16 during refluxing passes through line 72 to line 38 for return to tank 32 for additional system recycling. During the fractionation process condensed water and acetic acid pass through bottom line 62 and into collection tank 64. The separate recyclings and tap-offs are preferably operated on a continuous or semicontinuous basis and are controlled by conventional valving means (not shown) and the like in order to effect the best possible fractionation while minimizing steam consumption. Thus, when temperature at the top of column 16 reaches a level of about 148° F., columns 14 and 16 have been essentially purged of acetic acid and primary stage 10 is essentially filled with methanol.

At this point, steam is introduced through line 50 to the bottom of column 14 and allowed to pass upwardly therethrough with recycling via lines 26, 28 and reboiler 46. This steam purging has the effect of removing the methanol from column 14 (which is evidenced by a gradual rise in the temperature of the tower effluent leaving through line 34 from 148° to 212° F.). This effluent passes through condenser 36 and line 38 to feed tank 32 with a methanol-rich portion of this feed being tapped off for return to methanol tank 42 through line 40. The methanol-water mixture collected in tank 32 leaves the latter via line 52 and enters column 16 and is refluxed therein. As a consequence, the temperature of the effluent leaving column 16 through line 66 during the refluxing gradually rises from 148° to 212° F. as the system is progressively purged of methanol. At the same time, condensed water is allowed to pass through line 62 for collection with the acetic acid in tank 64. During this refluxing period, methane is recycled through lines 66, 73 with a methanol-rich portion being tapped off through lines 69 and 74 for return to tank 42. When the effluent temperature at the top of column 16 reaches approximately 212° F., the entire primary stage 10 has been cleared of alcohol with a mixture of water and acetic acid being collected in tank 64.

In sum therefore, the initially adsorbed acetic acid is first substantially converted to methyl acetate during regeneration operations, with this methyl acetate being reconverted to acetic acid and methanol according to the reversible reaction MeOH + HOAc ⇌ MeAc + H$_2$O during fractionation and steam purging. The driving force for such reconversion results from the progressive removal of methanol during the fractionation and purging, along with the addition of water.

In practice, an initial condensate feed stream containing approximately 0.2% by weight acetic acid can be concentrated in primary stage 10 to the extent that the mixture within tank 64 is approximately 5% by weight acetic acid, which of course amounts to a 20-fold concentration.

The acetic acid-water mixture collected within the tank 64 is then directed through line 76 to the top of carbon column 18 in secondary concentration stage 12. The mixture is then allowed to descend through the column in the normal manner whereupon the acetic acid fraction adsorbs on the carbon with a clarified feed which is essentially water exiting through line 80.

At this point ethanol from tank 92 is directed through line 106 through steam-fired reboiler 100 (in order to vaporize the ethanol) to the bottom of column 18. As the vaporized ethanol ascends through the column, vaporized ethyl acetate is formed and since this is the most volatile component, it, along with a fraction of vaporized ethanol, passes out the top of column 18 through line 84. Initially the temperature of the mixture leaving line 84 will be at a level of approximately 158° F., which indicates that it is primarily an azeotropic mixture of ethyl acetate, ethanol and water. As the level of vaporized ethanol rises in column 18 however, this temperature increases to a level of about 173° F. which signifies that essentially all of the acetic acid within column 18 has been converted to ethyl acetate.

The ethyl acetate-ethanol-water mixture in line 84 passes through heat exchanger 86 wherein it is condensed. Subsequent to this condensation, the mixture passes through line 88 and ultimately to fractionation column 20. At the same time, descending condensed acetic acid, ethanol and water pass through line 95 and into tank 96. This material is recycled through lines 98, 106, bypass 102 and line 104 to the top of column 18 in order to maximize the production of ethyl acetate which leaves column 18 through line 84 as explained.

In column 20 a refluxing takes place by virtue of the steam produced in reboiler 120. This steam ascends through fractionation column 20 and refluxed with the product entering the column through line 88. The initial effluent leaving top tower 20 through line 108 again consists of an azeotropic mixture of ethyl acetate, ethanol and water and is at a temperature of approximately 158° F. This mixture passes through heat exchanger 110 where it is condensed, and is recycled as necessary through line 112. As refluxing continues, ethyl acetate is continually removed via line 108 and the ethanolrich portion of the column effluent is directed through lines 104, 94 back to tank 92. At the same time, any acetic acid leaving bottom of column 20 through line 113 passes through lines 114 and 95 back to recycle tank 96 where it is again recycled through the system for the production of ethyl acetate. Also, excess water from the system is diverted through lines 112 into tank 124 for disposal through line 126.

Thus, in sum the apparatus of second stage 12 has the effect of maximizing the production of concentrated ethyl acetate. In particular, ethyl acetate is removed from line 108 while excess water is simultaneously removed from the system. This has the effect of driving the reversible reaction HOAc + EtOH ⇌ EtAc + H$_2$O to the right in order to maximize the production of concentrated ethyl acetate.

As explained, when the effluent leaving column 20 through line 108 is at a temperature of about 173° F., the entire second stage is substantially filled with ethanol and all of the ethyl acetate has been recovered.

The following example will illustrate the use of the present embodiment:

EXAMPLE I

A stream of sulfite process waste condensates comprising condensed digester relief and blow gases, as well as the condensates derived from the evaporation of spent pulping liquor, is analyzed to contain the following:

TABLE 1

| Waste Liquor Constituents | % By Weight | Feed Rate (lb/hr) |
|---|---|---|
| methanol | 0.13 | 124 |
| furfural | 0.07 | 72 |
| acetic acid | 0.61 | 602 |
| sulfur dioxide | 0.01 | 10 |
| water | 99.18 | 97,892 |
| TOTAL | 100.00 | 98,700 |

This stream is continuously passed through a primary stage carbon column having 80,000 pounds of activated carbon therein for a period of 12 hours. The clarified effluent from this passage contains essentially 124 lb/hr methanol and 97,892 lb/hr water, with trace quantities of acetic acid and sulfur dioxide. No furfural is detected.

At the end of the 12 hour treatment period of the activated carbon contains approximately the following:

TABLE 2

| Constituents | Pounds |
|---|---|
| furfural | 864 |
| acetic acid | 7,224 |
| sulfur dioxide | 120 |
| $^1$water | 71,792 |
| TOTAL | 80,000 |

$^1$This figure is derived by subtracting the total of the adsorbed non-aqueous constituents from the total number of pounds (80,000) of carbon since the latter will adsorb water approximately on a pound for pound basis.

At this point activated carbon is regenerated by passing vaporized methanol at 3,768 lb/hr for 7 hours through the primary stage carbon column. In particular, the methanol was passed for three hours down the column, and thereafter for four hours upwardly through the column. During the upflow period liquid methanol is fed into the top of the carbon column. Once the temperature of the liquid in the bottom of the carbon column reaches 150° F. and stays at this level for approximately 15 minutes, the methanol is purged from the first stage carbon column with direct steam at the rate of 5,000 lb/hr. The purged methanol is returned to the methanol regeneration tank either directly from the first carbon column condenser or from the top of the series coupled fractionation column.

The sulfur dioxide within the condensates reacts with some furfural, acetic acid and methanol to form polymerized material which is no longer volatile. This material leaves the bottom of the primary stage fractionation column with the other relatively less volatile materials, giving a supply in the fractionation column collection tank comprising:

TABLE 3

| Constituents | Pounds | % By Weight |
|---|---|---|
| furfural | 864 | 1.08 |
| acetic acid | 7,224 | 9.03 |
| polymerized material | 120 | 0.15 |
| water | 71,792 | 89.74 |
| TOTAL | 80,000 | 100.00 |

Thus, it will be seen that the primary stage treatment has the effect of concentrating the acetic acid from a level of about 0.61% by weight of about 9.03% by weight, which amounts to almost a 15-fold concentration.

It has been determined that the gallons per minute of evaporator condensate processed per lb of activated carbon remains constant in the concentration range of from about 0 to 1.0% by weight of the above adsorbed chemicals, and that one pound of activated carbon will remove all furfural, sulfur dioxide and acetic acid from about 1.74 gallons of sulfite evaporator condensate feed. Thus, since 80,000 lb condensates equals about 9,600 gal. of feed 9,600 gal. divided by 1.74 gal. per lb of carbon equals 5,520 lb of carbon which should be required to process the supply from the primary fractionation column. However, 16,000 lbs. of activated carbon is used in the second stage carbon column to illustrate the advantages of concentrating by using activated carbon.

Knowing activated carbon holds approximately its weight of this processed liquid, the carbon loading within the second stage is:

TABLE 4

| Constituents | Pounds | % By Weight |
|---|---|---|
| furfural | 864 | 5.40 |
| acetic acid | 7,224 | 45.15 |
| polymerized material | 120 | 0.75 |
| water | 7,792 | 48.70 |
| TOTAL | 16,000 | 100.00 |

The second stage carbon is regenerated by passing ethanol (instead of methanol) therethrough in order to convert the adsorbed acetic acid to ethyl acetate. Since the carbon's acetic acid loading is concentrated (45% by weight or higher), vaporized ethanol is added preferably to the bottom of the carbon column to regenerate effectively the carbon and take full advantage of the heat generated by the reaction of ethanol and acetic acid to form ethyl acetate and water. Approximately 1130 lb/hr of vaporized ethanol is used for 7 hours, (1 hour downflow and 6 hours upflow) to regenerate the carbon.

The overhead ethyl acetate product from the second stage carbon column is further recycled and concentrated in the second stage fractionation column in the conventional manner with the recovery of ethyl acetate as its tertiary azeotrope with ethanol and water having the following compositions:

TABLE 5

| Constituents | Pounds | % By Weight |
|---|---|---|
| ethyl acetate | 10,595 | 83 |
| ethanol | 1,149 | 9 |
| water | 1,021 | 8 |
| TOTAL | 12,765 | 100 |

After the recovery and concentration of ethyl acetate excess ethanol is returned from the top of the second stage carbon column and/or fractionation column. The following comprises the fractionator bottoms:

TABLE 6

| Constituents | Pounds | % By Weight |
|---|---|---|
| polymerized material | 120 | 1 |
| furfural | 864 | 9 |
| water | 8,938 | 90 |
| acetic acid | trace | |
| ethanol | trace | |
| TOTAL | 9,922 | 100.0 |

Approximately 6,687 lb of ethanol is used as makeup in this step.

This example demonstrates the advantages of the instant invention in producing a crude ethyl acetate and furfural product. It will be appreciated that continuous operations using the above method may require two or more activated carbon columns at each adsorption stage, and several distillation or fractionation columns to produce salable ethyl acetate and furfural products. The number of columns and fractionators are of course to be determined by the desired purity of the end products and the volume of feed to be handled.

Figure 2:
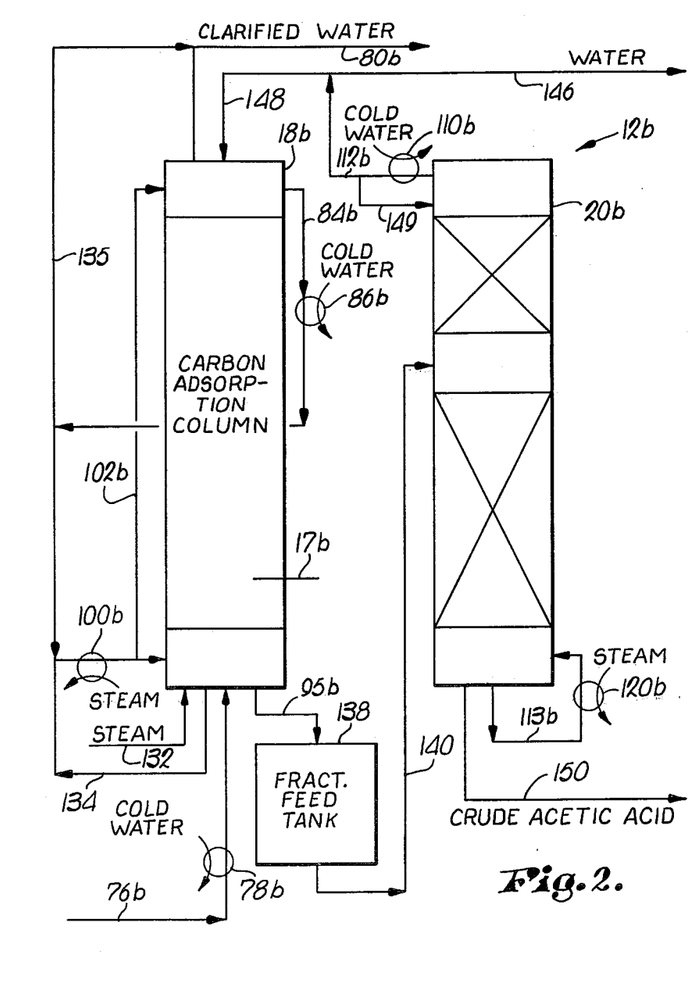
FIG. 2 is a schematic representation illustrating the use of stream as a carbon regenerating agent in secondary concentration stage of apparatus for producing a concentrated supply of acetic acid from dilute sulfite pulp-making condensates.

FIGURE 2 EMBODIMENT

The embodiment depicted in FIG. 2 is similar in many respects to that shown in FIG. 1, but in this instance a twostage concentration apparatus is provided for the production of crude acetic acid from sulfite pulp-making condensate liquors. In fact, the primary section 10 of FIG. 1 is identical in all respects with that to be used with the FIG. 2 embodiment, and accordingly a depiction of the first stage apparatus has been omitted from FIGS. 2 and 3. Furthermore, the operation of the first stage in each of the following embodiments is essentially the same as that in primary stage 10 of FIG. 1. Accordingly, in the interests of brevity, the operation of the first stage will not again be repeated in detail, and what follows immediately hereunder is a description of the apparatus and operation of the second concentration stage in the FIG. 2 apparatus.

Briefly, the apparatus of FIG. 2 includes the secondary concentration stage 12b which has an activated carbon adsorption column 18b in series with a fractionation column 20b. A feed line 76b from the collection tank of the primary stage (not shown) passes through a heat exchanger 78b and is cooled and connected to the bottom of column 18b. A clarified feed line 80b extends out the top of column 18b for the purpose of conveying clarified materials for disposal or reuse. External steam is provided through a line 132, and a recycle loop 134 is provided in conjunction with a steam-fired reboiler 100b providing the option for using direct and/or indirect steam. A line 102b extends from line 134 on the output side of reboiler 100b to the top of column 18b as depicted.

In addition, a line 84b extends from the top of column 18b and passes through heat exchanger 86b and ultimately interconnects with line 134 on the source side of reboiler 100b. Finally, a line 95b is connected to the bottom of tower 18b and communicates with collection tank 138. A line 135 also is connected between the end of line 84b and line 80b as illustrated.

A feed line 140 extends from tank 138 to the center of fractionation column 20b. The latter includes an effluent line 112b passing through a condenser 110b and ultimately interconnecting with water line 146. In addition, a recycle line 149 is connected to line 112b on the output side of the condenser 110b for recycling back to the top of column 20b. Also, a leg 148 of line 146 extends back to the top of column 18b as illustrated.

The bottom of column 20b is provided with a crude acetic acid product line 150 and a steam recycle loop 113b having a steam-filled reboiler 120b interposed therein.

In operation, feed comprising acetic acid, furfural, and water which has been concentrated in the primary stage of the apparatus is directed through line 76b and heat exchanger 78b to the bottom of column 18b. This feed follows an ascending path of travel through the activated carbon within column 18b so that substantially all the acetic acid, furfural and other materials adsorb on to the carbon, with the clarified water exiting through line 80b at the top of the column.

At this point, external steam is directed through line 132 to the bottom of column 18b whereupon the steam travels upwardly through the column and starts to regenerate and purge the adsorbed acetic acid. Of course, this operation could also be accomplished by downflowing steam as well. In any event, the desorbed acetic acid and water as a liquid is recycled through line 134 and vaporized in reboiler 100b prior to return to the bottom of column 18b. Any acetic acid and water vapor which initially rises to the top of column 18b is recycled back to the bottom of column 18b through lines 84b (which passes through condenser 86b) line 134 and reboiler 100b. This has the effect of recycling and concentrating the acetic acid for delivery to tank 138 via line 95b. In addition, the condensed acetic acid and water from the bottom of column 18b which are simultaneously recycled through loop 134 and reboiler 100b provides additional system vapor. A portion of this reboiler vapor is initially directed to the top of column 18b via line 102b to provide additional vapor action within the column to assist in purging liquid from the activated carbon.

In any event, during continuing operations condensed acetic acid and water travel through line 95b to feed tank 138, whereupon the mixture travels through line 140 to fractionation column 20b. At this point steam generated by reboiler 120b at the bottom of column 20b begins separating the crude acetic acid which leaves the bottom of the column through line 150.

Separated water and steam leaves the top of the tower through line 112b and passes through condenser 110b and ultimately out of the system via line 146. During the early stages of fractionation of course, the effluent leaving through line 112b can be recycled through line 148 or 149 in order to assure complete removal of the acetic acid from the system. It will be appreciated from the foregoing that in the operation of this embodiment there is no conversion acetic acid to methyl acetate with consequent reconversion of the latter and accordingly the operation of the FIG. 2 is somewhat simpler.

EXAMPLE II

As discussed above, the apparatus and process depicted and described in connection with primary stage 10 of FIG. 1 is identical in all respects with the primary stage to be used with the FIG. 2 embodiment. Moreover, the adsorption operation of column 18b in section 12b of FIG. 2 is identical to that of column 18 of FIG. 1, with the exception that the feed enters at the bottom and leaves the top of Column 18b. In particular, 80,000 lb of partially concentrated condensate feed having the composition as set forth in Table 2 is fed via line 76b to column 18b, which holds 16,000 pounds of activated carbon. This carbon adsorbs 16,000 lb of the feed liquid over a 12 hour period such that the adsorbed materials comprise:

TABLE 7

| Constituents | | Pounds | % By Weight |
|---|---|---|---|
| furfural | | 864 | 5.40 |
| acetic acid | | 7,224 | 45.15 |
| polymerized material | | 120 | 0.75 |
| water | | 7,792 | 48.70 |
| | TOTAL | 16,000 | 100.00 |

In this case steam (rather than methanol or ethanol), is used as the carbon regenerating agent, and the steam is introduced into column 18b at the bottom thereof at the rate of approximately 500 lb/hr. As the steam displaces the adsorbed materials held by the carbon, the liquid by gravity falls to the bottom of the carbon column and is recycled through line 134 and reboiler 100b. The direct introduction of steam is then discontinued, and the falling liquid is volatized in reboiler 100b using indirect steam. The vapor derived from reboiler 100b is initially directed via line 102b to the top of carbon column 18b. This has the effect of displacing any residual adsorbed materials which pass through line 95b and are collected in fractionator feed tank 138. These materials are then fed to the fractionation column 20b. Approximately equal quantities of the first portion of the fractionation column overheads are refluxed through lines 112b, 149 back to the top of the column and removed as a furfural water crude. The latter is treated for removal of the furfural fraction therefrom and equal quantities of the recovered water are refluxed and directed to the top of column 18b via line 148. The crude acetic acid product is also removed as column bottoms during the fractionation procedure. As the regeneration continues, direct steam is used intermittently in order to maintain liquid levels. Approximately 2,000 lb/hr of direct steam are used in a 12 hour regeneration period. The fractionation column bottom liquid comprises:

TABLE 8

| Constituents | | Pounds | % By Weight |
|---|---|---|---|
| acetic acid | | 7,224 | 85.0 |
| polymerized material | | 120 | 1.4 |
| water | | 1,156 | 13.6 |
| | TOTAL | 8,500 | 100.0 |

The removed condensed overhead comprised:

TABLE 9

| Constituents | Pounds | % By Weight |
| --- | --- | --- |
| furfural | 864 | 9.1 |
| water | 8,636 | 90.0 |
| TOTAL | 9,500 | 100.0 |

The condensed overhead separates into two layers, particularly at the start of the regeneration process. The top layer predominates and contains about 12% by weight furfural, while the bottom layer contains about 92% by weight furfural.

Figure 3:
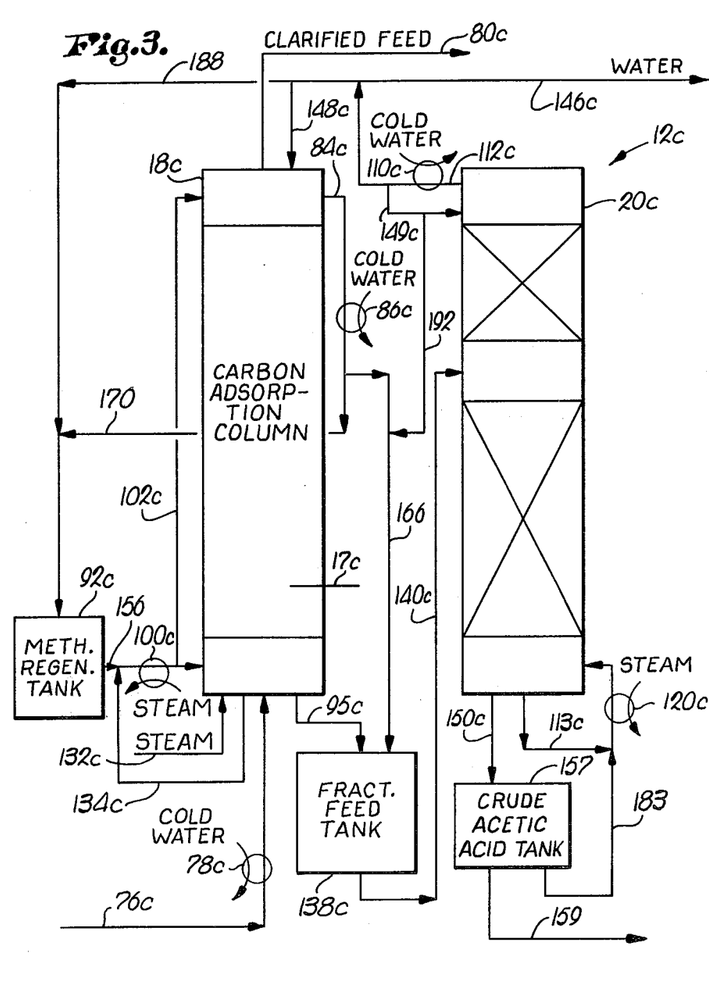
FIG. 3 is a schematic representation of the secondary concentration stage of apparatus similar in many respects to that shown in FIG. 1 but illustrating the use of methanol-steam as carbon regenerating agents.

FIGURE 3 EMBODIMENT

The second stage apparatus illustrated in FIG. 3 is also adapted for the production of concentrated crude acetic acid. In general, this apparatus is identical with primary stage 10 of FIG. 1 so that the resultant two-stage apparatus of FIG. 3 amounts essentially to two identical stages 10 coupled in series for concentrating acetic acid from sulfite pulpmaking condensates.

In more detail, the second stage apparatus 12c of FIG. 3 includes an activated carbon adsorption column 18c and a series-coupled fractionation column 20c. A feed line 76c extends from the carbon adsorption feed tank (not shown) associated with the primary stage and passes through exchanger 78c and is interconnected to the bottom of column 18c. A clarified feed line 80c is connected to the top of column 18c for the purpose of conveying clarified liquid for reuse or dumping. A methanol regeneration tank 92c is provided with a lower regeneration line 156 which passes through a steam-fired reboiler 100c. A line 102c is connected to line 156 on the output side of reboiler 100c and leads to the top of column 18c as depicted. In addition, a loop recycle line 134c is connected to the bottom of column 18c and line 156 on the source side of reboiler 100c. An external steam line 132c is also connected to the bottom of column 18c in order to purge the latter.

A product line 84c is connected to the top of column 18c and passes through a condenser 86c. A product line 166 is connected to line 84c and extends to feed tank 138c. In addition, an extension 170 of line 84c is provided for recycling back to generation tank 92c. A product line 95c is also connected to the bottom of column 18c and extends to feed tank 138c.

A fractionation column feed line 140c is interconnected between tank 138c and the central portion of tower 20c for the purpose of feeding product to the latter for separation. A crude acetic acid recovery line 150c is connected to the bottom of column 20c for conveying the concentrated crude acetic acid to tank 157. A line 159 is also provided for conveying the acetic acid for further purification, which may be accomplished using additional fractionation columns or the like. In addition, a steam loop 113c having a steam-fired reboiler 120c interposed therein is situated in the bottom of column 20c for producing fractionation vapors. A line 112c is attached to the top of column 20c and has a cold water condenser 110c interposed therein. Line 112c is connected to water recovery line 146c for the purpose of conveying recovered water from the process, and also to methanol return line 188 which is interconnected with line 170 and extends to regeneration tank 92c. A tap-off 148c from line 188 extends to the top of adsorption column 18c to provide recycling as required. Finally, a recycle line 149c is connected to line 112c on the output side of condenser 110c and extends back to the top of column 20c. A line 192 is connected at respective ends thereof to line 149c and 166, the latter of which is in connection with feed tank 138c.

In use, stage 12c receives acetic acid and water concentrated in the first stage via line 76c for upward travel through column 18c and adsorption of the acetic acid on the activated carbon therewithin. A clarified feed consisting of water and a minor proportion of methanol exits through line 80c in the normal manner.

After adsorption, methanol from tank 92c is vaporized in reboiler 100c and directed through line 102c to the top of column 18c whereupon the vaporized methanol descends through the column. This is continued until the methanol level reaches an appropriate point near the bottom of column 18c as measured by a temperature probe 17c. The methanol level can be detected by a temperature of approximately 150° F. at probe 17c. At this point vaporized methanol is directed for upward travel through column 18c and methyl acetate (which is the most volatile component) along with a portion of the volatilized methanol pass through line 84c and are condensed in condenser 86c and ultimately passed through line 166 to tank 138c or through line 170 to methanol regeneration tank 92c. Condensed methanol, water and acetic acid pass through line 95c to tank 138c.

Simultaneously with delivery of vaporized methanol to the bottom of column 18c, condensed methanol from fractionation column 20c is fed through line 148c to the top of column 18c in order to give a refluxing action within column 18c which assures greater product separation and recovery. During such refluxing additional vaporized methyl acetate and methanol pass through line 84c, condenser 86c and ultimately to tank 138c, while condensed methanol, water and acetic acid travel through line 95c to tank 138c. The effluent leaving line 84c at the top of column 18c is initially at a temperature of 128° F. which signifies that the mixture is primarily methyl acetate. During the regeneration treatment with vaporized methanol however, this temperature gradually rises until it reaches the level of about 150° F. at which point substantially all of the adsorbed acetic acid has been removed from column 18c.

The aqueous methanol-methyl acetate mixture within tank 138c passes via line 140c to fractionation column 20c which is vaporized by provision of steam loop 113c and reboiler 120c. The mixture from feed line 140c is refluxed within column 20c in order to separate out the acetic acid fraction and cause reconversion of the methyl acetate to methanol and acetic acid, all as explained in connection with the FIG. 1 embodiment. This methanol is then returned to tank 92c for reuse. In particular, the initial product leaving column 20c through line 112c is at a temperature of approximately 128° F., again signifying the presence of methyl acetate. During continued refluxing however, the level of vaporized methanol rises within the tower 20c is evidenced by gradual rise in temperature of the mixture leaving the column to a level of approximately 150° F. In any event, during such refluxing before the final temperature is reached, a portion of the mixture is recycled through line 149 while the other portion is fed via line 112c and 148c for recycling through the system, while a methanol fraction from line 84c is returned via lines 170, 188 to tank 92c. In addition, an appropriate portion of the product mixture leaving column 18c during refluxing passes through line 192 for additional system recycling. During the fractionation process, condensed water and acetic acid pass through bottom line 150c and are collected in tank 157. When the temperature at the top of column 18c reaches a level of about 150° F., column 18c and 20c have been essentially purged of acetic acid and stage 12c is essentially filled with methanol.

At this point, steam is introduced through line 132c and allowed to pass upwardly through column 18c with recycling via lines 134c, 156 and reboiler 100c. This steam purging has the effect of removing the methanol from column 18c (which is evidenced by a gradual rise in the temperature of the tower effluent leaving through line 84c from 150° to 212° F.). In initial stages, the methanol-rich portion of the overhead is tapped off and returned to tank 92c through line 170. This is continued until the overhead temperature reaches about 175° F., at which point the overhead passes through condenser 86c and line 166 to tank 138c. The methanol-water mixture collected in tank 138c leaves the latter by way of line 140c and enters column 20c and is refluxed therein. As a consequence, the temperature of the effluent leaving column 20c gradually rises from 150° to 212° F. as the system is progressively purged of methanol. The crude acetic acid tank 157 is provided to facilitate the complete purging of methanol, the production of a furfural water crude and the further concentration of the crude acetic acid by recycling it through lines 150c, 113c and 183. The crude acetic acid product leaves the system through line 159. The furfural water crude leaves stage 12c via line 112c and 146c, and when the effluent from column 20c reaches and remains at approximately 212° F., stage 12c has been essentially cleared of the alcohol and furfural-water crude.

EXAMPLE III

This example is identical in every respect to Example II, save for the use of methanol as a regenerating agent instead of steam. In essence, operation of the present embodiment involves a dual treatment of sulfite condensates in accordance with the method described in connection with primary stage 10 of FIG. 1. In particular, second stage column 20c again holds 16,000 lb of activated carbon, which in turn permits adsorption of about 7,224 lb of acetic acid less methanol. Approximately 750 lb/hr of regeneration methanol is employed in a manner such that methyl acetate production is kept to a minimum. This is accomplished by contacting the activated carbon with vaporized methanol for 7 hours, 6 hours downflow and 1 hour upflow, to regenerate the carbon. The methyl acetate produced during this regeneration combines with water and acetic acid in the fractionation feed tank and is fed into the fractionation column at a packed height advantageous to reconvert it back to acetic acid and methanol. The methyl acetate and methanol is recycled from the fractionator back to the methanol regeneration tank, where during upflow conditions it is combined with water in the bottom of the carbon column to further enhance reconversion to methanol and acetic acid. The latter is facilitated by controlling the temperature at the feed point of the fractionation column and at temperature probe 17c in the carbon column at 210° F. Once the temperature at the top of both columns reach 150° F., steam is introduced via line 132c at approximately 500 lb/hr. to purge the methanol from the system. When the temperature at the top of the carbon column reaches 212° F. and the temperature at the top of the fractionation column reaches 150° F., the carbon will have substantially completely purged and reactivated. The methanol is then purged from the fractionation column back to the methanol regeneration tank by recycling crude acetic acid from the crude acetic acid tank. After the methanol has been purged from the fractionator, the crude acetic acid is concentrated by removing a furfural-water crude as overhead. The acetic acid and furfural crudes will comprise substantially the same quantities and constituents as produced in Example II (Tables 8 and 9), except the furfural crude fraction will contain a minor amount of methanol.

Figure 4:
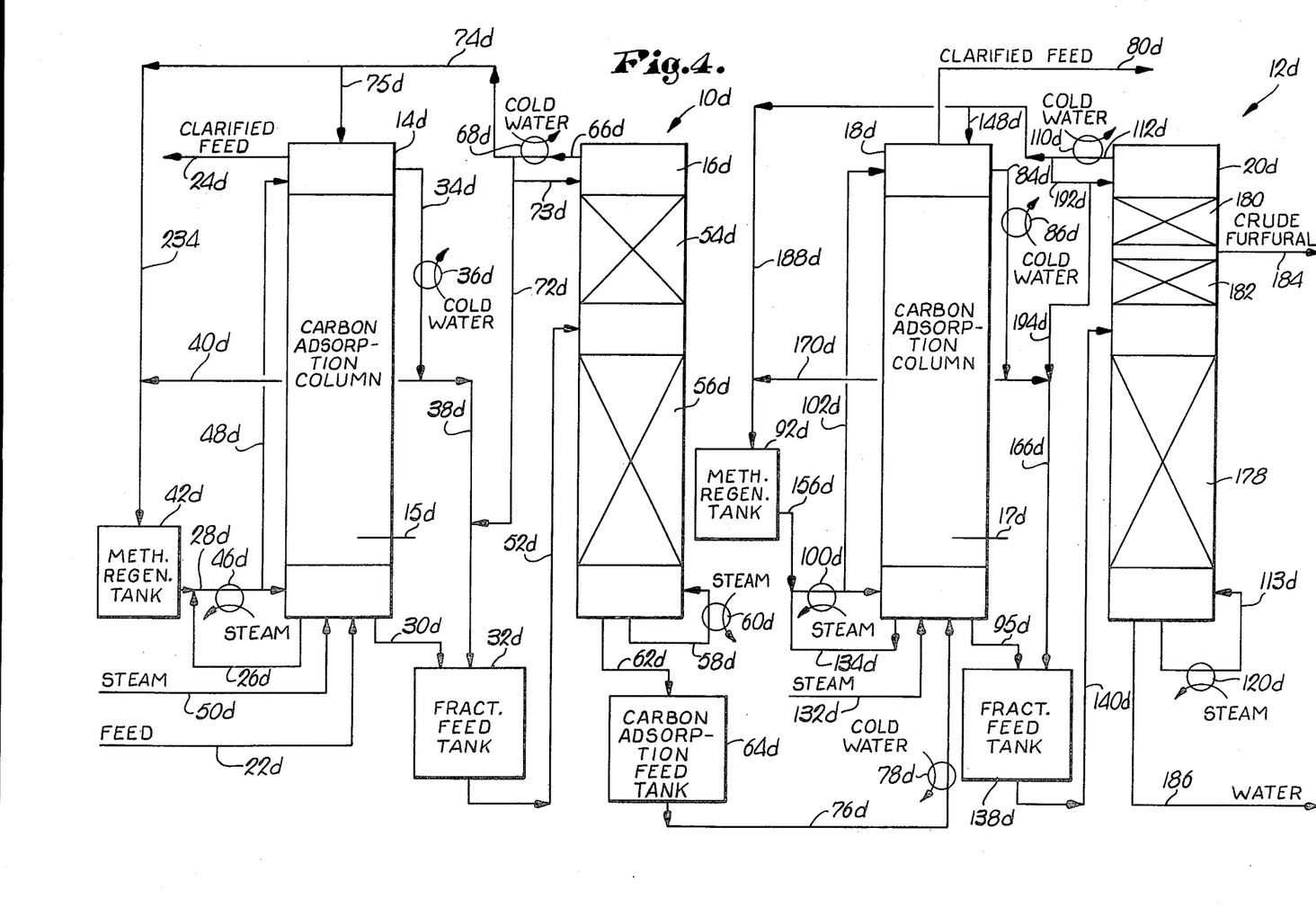
FIG. 4 and 5 are schematic representations illustrating two types of apparatus in accordance with the invention for the production of concentrated supplies of furfural from dilute sulfite waste condensates.

FIG. 4 EMBODIMENT

This embodiment of the present invention is particularly adapted for the recovery of furfural from a sulfite pulp-making waste condensate which also contains fractions of methanol, acetic acid, sulfur dioxide and water. Broadly, the apparatus in FIG. 4 includes a primary adsorption and concentration stage 10d coupled with a secondary adsorption and concentration stage 12d. Primary stage 10d includes carbon adsorption column 14d and a series-connected fractionating column 16d, while secondary stage 12d likewise has an activated carbon column 18d and a specialized fractionation column 20d.

Activated carbon column 14d (having a temperature probe 15d) is of conventional variety and is filled with activated carbon which is operable to adsorb the furfural component (along with any polymerized material) from the condensate feed stream. A feed line 22d is provided at the bottom of column 14d for the introduction of waste condensate into the column, with an exit line 24d at the top of the ladder for conveying clarified feed. In addition, a line 26d is connected to the bottom of column 14d to provide a recycle which is connected to methanol regeneration line 28d as depicted. A product line 30d also is connected to the bottom of column 14d and extends to fractionation column feed tank 32d. An upper product line 34d is connected to the top of column 14d and extends through heat exchanger 36d. A line 38d is interconnected between line 34d and tank 32d, along with a recycle line 40d interconnecting line 234 and methanol regeneration tank 42d. Regeneration line 28d extends between tank 42d and the bottom of column 14d, and passes through a steamfired reboiler 46d. A line 48d is connected to line 28d between reboiler 46d and column 14d and extends to the top of the latter as shown. Finally, a steam line 50d is provided for conveying steam to the bottom of column 14d during purging operations.

A fractionation column feed line 52d is connected to the bottom of tank 32d and extends to the midportion of fractionation column 16d between the spaced packing section 54d and 56d therein. A steam cycle line 58d is connected to the bottom of column 16d and passes through a steam-fired reboiler 60d. Furthermore, a recovery line 62d extends between the bottom of column 16d and collection tank 64d. A line 66d extends from the top of column 16d and passes through condenser 68d, with the remaining end of line 66d being connected to line 74d which is ultimately connected to regeneration tank 42d through line 234. A tap-off 75d extends from line 74d to the top of carbon column 14d for the purpose of providing system recycling. Furthermore, a line 72d extends from line 66d on the output side of condenser 68d and is connected to line 38d leading feed tank 32d. Finally, a recycle line 73d is connected to line 72d and extends back to the top of fractionation column 16d.

A feed line 76d extends from tank 64d to the bottom of secondary adsorption column 18d with a heat exchanger 78d being interposed in the line to cool the feed. The clarified feed line 80d is connected to the top of column 18d for the purpose of conveying clarified feed for disposal or reuse. A product recovery line 84d is connected to the top of column 18d and passes through a condenser 86d and is ultimately connected to line 166d which in turn is connected to feed tank 138d. A recycle line 170d is also connected to line 84d and this extends for connection with line 188d leading to methanol regeneration tank 92d. A product recovery line 95d is connected to the bottom of column 18d and extends to feed tank 138d as illustrated. In addition, a steam purging line 132d is connected to the bottom of column 18d, with a recycle line 134d likewise being connected to the bottom of the column and having steam-fired reboiler 100d interposed therein. A methanol regeneration line 156d is connected at respective ends thereof to methanol regeneration tank 92d and line 134d, with a secondary regeneration line 102d being connected to line 134d on the output side of the reboiler and extending to the top of column 18d.

A feed line 140d is connected to tank 138d and extends to the midportion of fractionation column 20d. The latter includes a lowermost packing section 178 and a pair of uppermost sections 180 and 182 respectively. A crude furfural tap-off line 184 is provided between the upper packing sections for the purpose of removing a side cut of product from the system. In addition, a line 112d extends from the top of the column 20d and passes through condenser 110d. A recycle line 192d is connected to line 112d and extends back to the top of column 20d in the normal manner. Line 112d is also connected to line 188d which ultimately leads back to methanol regeneration tank 92d, with a tap-off recycle line 148d being provided for recycling to the top of carbon adsorption column 18d. Another line 194d extends from the recycle line 192d back to feed tank 138d in order to provide recycling. Finally, a water line 186 is connected to the bottom of column 20d in order to convey clarified water from the system, along with the steam loop 113d having a reboiler 120d interposed therein for generating indirect system steam.

In general, the operation of primary stage 10d corresponds to that of stage 10 of FIG. 1. Therefore, the operation of stage 10d will be described in detail only in the aspects thereof differing from stage 10.

Column 14d is preferably sized for absorbing furfural from a conventional sulfite condensate waste stream for a relatively long period, for example about 120 hours. In this regard, the acetic acid content of normal sulfite condensates will break through the column after a short time, e.g., about three hours, because of the much greater concentration thereof, but the adsorbed acetic acid will be progressively replaced with furfural over time. At the end of 120 hours, the carbon within column 14d will be substantially loaded with furfural with only a minor amount of acetic acid being present.

At this point vaporized methanol is started down the top of column 14d via lines 28d, 48d. By virtue of the fact that there is little acetic acid present in column 14d, there is little heat of reaction from the formation of methyl acetate. Therefore, downward travel of methanol is continued until the vapor breaks through adjacent bottom of column 14d, (as indicated by the temperature reading of probe 15d), whereupon upward travel thereof is commenced by delivery of addition quantities of methanol through line 28d. During downflow of methanol within column 14d, furfural, water, a minor amount of acetic acid and any polymerized materials present pass through line 30d to tank 32d, and any methyl acetate formed will condense as the column heats up and similarly be forced out of column 14d. The secondary upward travel of methanol vapor and downward travel of methanol liquid within column 14d completes the removal of furfural such that the column is essentially loaded with methanol. The originally adsorbed furfural is at this point collected in tank 32d.

The mixture within tank 32d is subsequently directed through line 52d to fractionation column 16d. This column serves in the well-known manner to separate the furfural and deliver the same to tank 64d while directing the recovered methanol back to tank 42d through lines 74d, 234. Since the recycle operation of column 16d is identical with that described in connection with previous embodiments, this description will not be repeated. Similarly, steam purging operations in connection with stage 10d are identical in all respects with that of earlier embodiments and will not be discussed herein.

In any event, the crude furfural, polymerized material and the like which have been partially concentrated within stage 10d is passed from tank 64d to carbon column 18d, whereupon the furfural is readsorbed. The two stage up-down vaporized methanol regeneration technique is followed which serves to deliver the adsorbed furfural to tank 138d. This furfural fraction is then delivered to fractionation column 20d for final recovery.

Column 20d is somewhat different than the columns of the previous embodiments in that a crude furfural side tap line 184 is provided. In this regard, as conventional fractionation proceeds within column 20d crude furfural (about 90% concentrated) is continually withdrawn through line 184 at a temperature of from about 208° to 210° F., with recovered methanol being directed via line 188d back to regeneration tank 92d. This side tap recovery technique is similar in some respects to that illustrated in U.S. Pat. No. 3,764,462. In other embodiments, use can be made of a batch fractionation column or two fractionation columns in series which would eliminate the need for this side cut.

The final step involves steam purging of stage 12d which is again accomplished in a well-known manner identical with that discussed in detail above.

EXAMPLE IV

The same sulfite process waste condensates as used in Example I are cooled and passed through 80,000 pounds of activated carbon contained in the first activated carbon column shown on FIG. 4 for approximately 120 hours. The effluent (clarified feed) contains essentially 124 lb/hr methanol, 602 lb/hr acetic acid and 79,274 lb/hr water with some sulfur dioxide in an organic combined form with acetic acid and/or methanol.

After the 120 hours period the activated carbon contains approximately:

TABLE 10

| Constituents | | Pounds |
| --- | --- | --- |
| furfural | | 8,640 |
| sulfur dioxide | | 1,200 |
| water | | 70,160 |
| | TOTAL | 80,000 |

This activated carbon is then regenerated with methanol as described above. Again the sulfur dioxide reacts with some furfural, acetic acid and methanol to form polymerized material which is no longer volatile. It leaves the bottom of the first fractionation column in a stream comprising:

TABLE 11

| Constituents | | Pounds | % By Weight |
| --- | --- | --- | --- |
| furfural | | 8,640 | 10.8 |
| polymerized material | | 1,200 | 1.5 |
| water | | 70,160 | 87.7 |
| | TOTAL | 80,000 | 100.0 |

As explained, furfural replaces acetic acid as the primary organic chemical being adsorbed in the present Example. It has been determined that the pressure drop across the activated carbon column increases rapidly at 15 to 22% by weight furfural carbon loadings, so the latter is the governing factor for carbon column height. For illustrative purposes 16,000 lb of activated carbon is used in the second activated carbon column. Since the carbon in the secondary stage column will hold approximately its weight in process liquid, the adsorbed chemicals will comprise:

TABLE 12

| Constituents | | Pounds | % By Weight |
| --- | --- | --- | --- |
| furfural | | 8,640 | 54.0 |
| polymerized material | | 1,200 | 7.5 |
| water | | 6,160 | 38.5 |
| | TOTAL | 16,000 | 100.0 |

These materials are desorbed in exactly the same manner as the first stage column, using methanol as the regenerating agent. However, the operation of the second stage fractionation column is somewhat different. First of all, methanol is recycled back to the methanol regeneration tank from the top of the column via lines 112d, 188d. A furfural side cut is continuously withdrawn from top 184 under the methanol at a column temperature of 208°–210° F. This side cut has approximately the following composition:

TABLE 13

| Constituents | | Pounds | % By Weight |
| --- | --- | --- | --- |
| furfural | | 8,640 | 92 |
| methanol | | 188 | 2 |
| water | | 563 | 6 |
| | TOTAL | 9,391 | 100 |

The effluent from the bottom of the fractionation column is analyzed to contain:

TABLE 14

| Constituents | | Pounds | % By Weight |
| --- | --- | --- | --- |
| polymerized material | | 1,200 | 17.7 |
| water | | 5,597 | 82.3 |

TABLE 14-continued

| Constituents | | Pounds | % By Weight |
| --- | --- | --- | --- |
| | TOTAL | 6,797 | 100.0 |

Approximately 188 lb of methanol is used as makeup in this Example.

In alternative procedures two or more fractionation columns can be used which would eliminate the need for the furfural side cut. In addition, extra fractionators could be designed to give a 99% by weight furfural product, and no methanol makeup would be required. These columns could be designed to separate methanol, furfural and water taken as an overhead product or water, furfural and polymerized material taken as the bottom product from the first fractionation column of the second adsorption stage.

Figure 5:
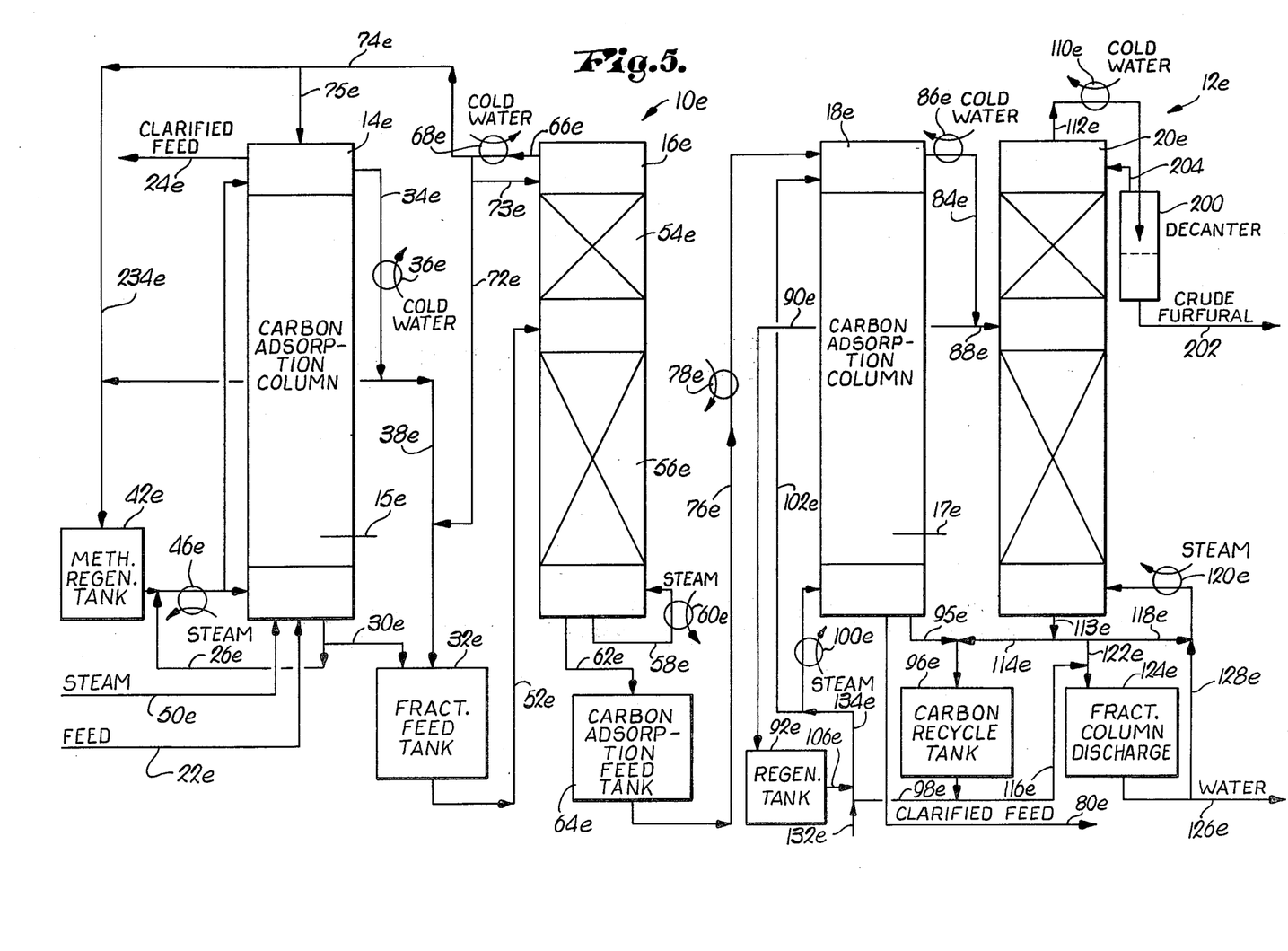

FIGURE 5 EMBODIMENT

This embodiment of the present invention is in many respects identical with that discussed above in connection with FIG. 4. In particular, the first stage apparatus 10e is in operation identical with stage 10d discussed in FIG. 4 and includes a carbon adsorption column 14e and a series-connected fractionation column 16e, along with the other apparatus discussed above. In this case, for ease of discussion the numerals used in FIG. 4 have been transferred to the present drawing but herein are denominated an e as opposed to a d. Thus, the discussion of the apparatus and operation of first stage 10e can be easily determined from the parallel discussion in connection with FIG. 4.

Secondary stage 12e includes an activated carbon adsorption column 18e and a series-related fractionation column 20e. Line 76e leading from primary stage tank 64e extends through condenser 78e to the top of column 18e for the purpose of delivering partially concentrated furfural liquid to the latter. A lower clarified feed line 80e is connected to the bottom of column 18e as illustrated and the latter also includes a lower temperature probe 17e.

A line 95e is interconnected between the bottom of column 18e and carbon recycle tank 96e. A line 98e extends from tank 96e and is connected to a line 134e which passes through steam-fired reboiler 100e and connects to the bottom of column 18e. A bypass line 102e is connected to line 134e on the source side of reboiler 100e and extends to the top of column 18e. An external steam line 132e is also connected to line 134e on the source side of reboiler 100e. A regeneration tank 92e is also provided in conjunction with secondary stage 12e, with a line 106e interconnected between tank 96e and line 134e.

A line 84e is connected to the top of column 18e and extends through cold water heat exchanger 86e and is ultimately connected to line 88e which is in turn connected to fractionation column 20e. A recycle line 90e is also connected to line 84e and extends to regeneration tank 92e as illustrated.

An overhead line 112e is connected to the top of fractionation column 20e and extends through cold water heat exchanger 110e and is ultimately connected to a conventional decanter 200. Decanter 200 includes a crude furfural product line 202 and a recycle line 204 which extends back to the top of column 20e to provide a recycle. The bottom of column 20e is provided with a line 113e which in conjunction with line 118e provides a steam loop passing through a steam-fired reboiler 120e. In addition, a line 114e is connected between line 113e and product delivery line 95e leading to tank 96e. A fractionation column discharge tank 124e is also provided, along with a line 122e connected between the latter and line 118e. A line 116e is connected between carbon recycle tank 96e and line 122e as depicted. Finally, a water line 126e is provided in conjunction with tank 124e, with a line 128e extending from line 118e to line 126e.

Following passage of partially connected furfural through column 18e in the manner described above, direct steam is introduced into the bottom of the column through lines 132e and 134e. As the carbon in the column is heated, the steam condenses. The condensed steam, along with the adsorbed liquid forced out of the carbon, are removed from the bottom of the column through line 95e into the carbon recycle tank 96e. From this tank it is fed through lines 98e and 134e and reboiler 100e back to the bottom of column 18e in a partially vaporized condition. This is accomplished by discontinuing the use of direct steam and using indirect steam derived from reboiler 100e. Probe 17e situated adjacent the bottom measures the vapor temperature and serves as monitor for regeneration procedures. The rising vapor forces the furfural as a vapor up through the carbon. Excess water and nonvolatile and/or polymerized material return to the carbon recycle tank 96e through line 95e. By conventional level controlling techniques this liquid is transferred to the fractionator column discharge tank 124e. From there it is recycled through line 128e and reboiler 120e to the bottom of the fractionation column 20e and lines 113e and 118e back to reboiler 120e. Indirect steam is used in reboiler 120e to vaporize the water and any furfural that may initially be in the bottom liquid from the adsorption column 18e and concentrate the nonvolatile material. This material is returned to the evaporator system for further concentrating, recovery and/or burning. THe vapors leave column 18e through line 84e into condenser 86e. After they are condensed, the condensate is fed into column 20e through line 88e. The vapors generated in reboiler 120e pass up the column and strip the furfural from the condensate. This furfural, along with water, leaves the top of fractionation column 20e through line 112e as a vapor. This vapor is condensed using indirect cooling water in condenser 110e and recovered in decanter 200. By allowing the temperature in the decanter to drop to room temperature (about 70° F.) the furfural composition in the water exceeds its solubility limits and separates into two phases. The high furfural phase, over 90% by weight furfural, is heavier than the high water phase, over 80% by weight water, and is removed from the bottom of the decanter 200 through line 202 for disposal or further purification. The water layer, saturated with furfural, is returned to the top of fractionation column 20e through line 204 for further treatment therein.

Once the furfural and polymerized material are removed from the carbon, water is removed from system 12e through line 90e into regeneration tank 92e. This water can be used to start the following carbon regeneration cycles instead of direct steam by feeding it through reboiler 100e via lines 106e and 98e. It can also be removed through the clarified feed line 80e via the same lines and not using indirect steam in reboiler 100e. Line 114e connects lines 113e and 95e so that both reboilers 100e and 120e can be used to concentrate the nonvolatile, polymerized material at the end of the carbon regeneration cycle.

As explained above, the operation of primary stage 16e is identical with that described in connection with FIG. 4. However, the operation of secondary stage 12e is somewhat different by virtue of the use of steam for carbon regeneration instead of alcohol and the use of decanter 200 for fural separation as opposed to a side tap.

EXAMPLE V

The same sulfite process waste condensates as used in Example I is processed as the present Example. The operation is identical with that described in connection with Example IV through the primary concentration stage of the adsorption step of the secondary stage.

The 16,000 lb of activated carbon in the secondary stage adsorption column holds:

TABLE 15

| Constituents | | Pounds | % By Weight |
|---|---|---|---|
| furfural | | 8,640 | 54.0 |
| polymerized material | | 1,200 | 7.5 |
| water | | 6,160 | 38.5 |
| | TOTAL | 16,000 | 100.0 |

This second stage is reactivated using methanol exactly as described in the FIG. 4 embodiment. The furfural removed from the decanter has the following composition:

TABLE 16

| Constituents | | Pounds | % By Weight |
|---|---|---|---|
| furfural | | 8,640 | 92.0 |
| water | | 751 | 8.0 |
| | TOTAL | 9,391 | 100.0 |

Finally, the effluent from the fractionation column discharge tank is:

TABLE 17

| Constituents | | Pounds | % By Weight |
|---|---|---|---|
| polymerized material | | 1,200 | 50.0 |
| water | | 1,200 | 50.0 |
| | TOTAL | 2,400 | 100.0 |

The water leaving with the clarified feed amounts to about 4,209 lb.

Figure 6:
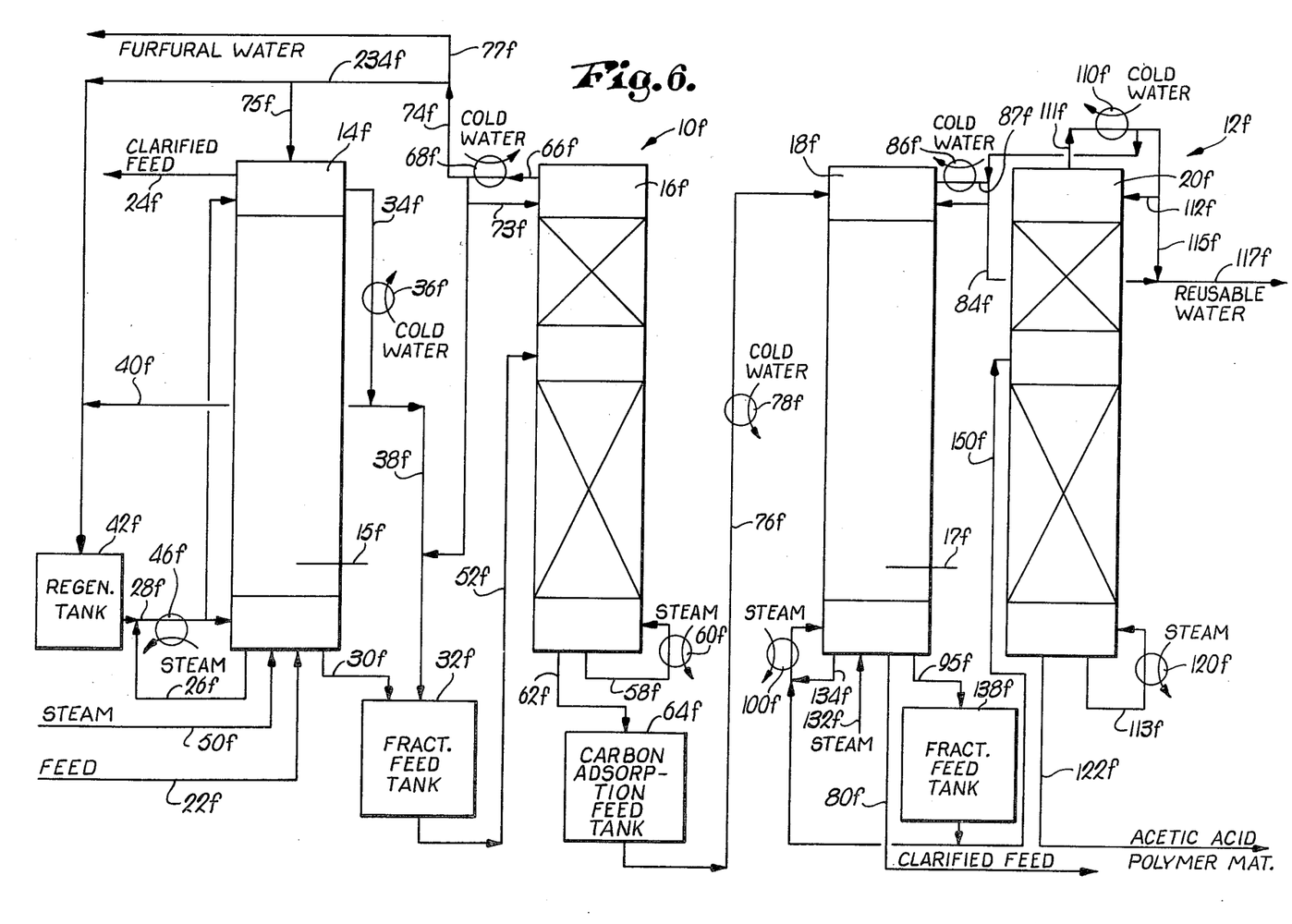
FIG. 6 is a schematic representation illustrating apparatus for the production of concentrated acetic acid from dilute sulfite pulp-making condensates wherein steam is employed as a regenerating agent in both the primary and secondary stages.

FIG. 6 EMBODIMENT

This embodiment of the invention is somewhat different from those previously presented in that steam is utilized to regenerate the activated carbon in both stages during production of concentrated acetic acid. Broadly, the apparatus of FIG. 6 comprises a primary adsorption and concentration stage 10f coupled with a secondary stage 12f operable to produce concentrated acetic acid. In the first stage, feed enters the bottom of carbon absorption column 14f through line 22f, and clarified feed leaves throough line 24f at the top. At this point regeneration steam is fed directly to the bottom of column 14f through line 50f. As the carbon is heated, the steam condenses. The condensed steam, along with the adsorbed liquid forced out of the carbon pores, are removed from the bottom of the column through line 30f into fractionation feed tank 32f. At the same time a portion of this liquid is vaporized by recycling through line 26f and reboiler 46f. This is accomplished by discontinuing direct steam, and using indirect steam derived from the reboiler. Probe 15f measures the vapor temperature and provides a monitoring function for the regeneration step. As the steam passes up column 14f it vaporizes furfural which likewise ascends through the column. Acetic acid, water and polymerized material flow on the other hand through line 30f into fractionation feed tank 32f.

The ascending furfural-water vapor passes through line 34f, is condensed in condenser 36f, and drops into tank 32f through line 38f. The liquid collected in this tank is fed through line 52f to the midsection of fractionation column 16f. The acetic acid and polymerized material are concentrated in column 16f by recycling through reboiler 60f via line 58f. Indirect steam is used in the reboiler to vaporize and concentrate the aqueous solution of these chemicals. The furfural-water vapors leave column 16f through line 66f and are condensed in condenser 68f. Initially these condensed vapors are recycled back to the top of this column through line 73f and are thereafter removed through line 77f for disposal or further concentration. Once the furfural has been removed from primary stage 10f, water is directed from column 16f through lines 74f, 234f, and from column 14f through 40f to tank 42f for recycling back through line 28f to column 14f. At the same time, a fraction of the overhead from column 16f is then recycled back to the top of column 14f through line 75f. Once acetic acid stops coming from the bottom of column 14f through line 30f, the carbon has been regenerated and ready for reuse. During the regeneration cycle excess water may be removed through line 77f.

During fractionation procedures the aqueous solution of acetic acid and polymerized material is discharged from the bottom of column 16f through line 62f into carbon adsorption feed tank 64f. From there it is fed through line 76f and heat exchanger 78f to the top of carbon adsorption column 18f for adsorption of the acetic acid content onto the carbon. The clarified feed leaves the bottom of this column through line 80f.

The steam regeneration of stage 12f involves directing steam via line 132f for passage upwardly through column 18f. Condensed steam and regenerated acetic acid are recycled through line 134f and reboiler 100f and ultimately pass out line 95f to tank 138f. The column overhead is recycled through loop line 87f and condenser 86f to the top of column 18f, with a tap off line 84f being provided for conveying excess water out of the system from the column overhead.

LIne 150f between tank 138f and fractionation column 20f is provided for directing the acetic acid-water mixture in tank 138f to the fractionator for concentrating. The latter is accomplished in the normal manner with concentrated acetic acid leaving as an underflow through line 122f. The water overhead leaves through line 111f and passes through condenser 110f. Initial stages the overhead is recycled through line 112f to the top of column 20f, and through lines 111f, 87f to the top of column 18f. As the acetic acid content of the overhead diminishes however, the water is directed through lines 115f, 117f for reuse or disposal.

EXAMPLE VI

Sulfite process waste condensates derived from condensed digester relief and blow gases, as well as the condensates derived from the evaporation of spent pulping liquor are processed in the FIG. 6 apparatus. The waste condensates have the same analyses as set forth in Example I. The first stage adsorption column contains 80,000 pounds of carbon and the condensates are passed therethrough for 12 hours at a feed rate of 98,700 lb/hr. After the 12 hour period the activated carbon contains approximately:

TABLE 18

| Constituents | Pounds |
| --- | --- |
| furfural | 864 |
| acetic acid | 7,224 |
| sulfur dioxide | 120 |
| water | 71,792 |
| TOTAL | 80,000 |

The adsorption process if of course identical to that in the first carbon adsorption column of Example I.

The activated carbon is regenerated by passing direct steam initially into the bottom of the carbon column at 2,120 lb/hr for about 1 hour. At this point indirect steam from the reboiler is used to vaporize the condensed steam and accumulated desorbed liquid. During the regeneration cycle a furfural-water solution is removed as overhead from the fractionation column for further furfural purification and recovery. This stream contains approximately 864 lb furfural and 10,600 lb water. From the bottom of this first stage fractionation column a liquid is removed which contains:

TABLE 19

| Constituents | Pounds |
| --- | --- |
| acetic acid | 7,224 |
| polymerized material | 120 |
| water | 63,312 |
| TOTAL | 70,656 |

When this partially concentrated supply of acetic acid passed through the second stage activated carbon adsorption system (containing 16,000 lb as in Example I), the carbon holds:

TABLE 20

| Constituents | Pounds | % By Weight |
| --- | --- | --- |
| acetic acid | 7,224 | 45.15 |
| polymerized material | 120 | .75 |
| water | 8,656 | 54.10 |
| TOTAL | 16,000 | 100.00 |

This second stage carbon is regenerated in a manner similar to the treatment of the carbon in the first stage. In this instance however, water is removed as overhead instead of a furfural-water solution, and 442 pounds of direct steam is used for the first hour, with indirect steam thereafter. 7,942 lb water are removed as overhead from the fractionation column, and the following is removed from the bottom thereof:

TABLE 21

| Constituents | Pounds | % By Weight |
| --- | --- | --- |
| acetic acid | 7,224 | 85.0 |
| polymerized material | 120 | 1.4 |
| water | 1,156 | 13.6 |
| TOTAL | 8,500 | 100.0 |

What is claimed as new and desired to be secured by Letters Patent is:

1. A method of continuously concentrating a dilute liquid supply of chemicals to provide a concentrated supply of end products, said method comprising the steps of:

continuously directing a stream of said dilute supply of chemicals through a primary concentration zone containing a first adsorption media, and adsorbing at least a portion of said chemicals on the first media;

thereafter passing a first eluant through the first media for desorbing at least a portion of the adsorbed chemicals and producing a stream comprising primary stage desorbed products and first eluant;

passing said stream of primary stage desorbed products and first eluant into a fractionation column coupled with said primary concentration zone, and treating the same to produce a supply of primary stage end products more concentrated than said dilute supply, and to separate at least a substantial fraction of the first eluant from said primary stage end products, said treating including the steps of refluxing said stream of primary stage desorbed products and said eluant within the column, recycling the refluxed stream as necessary through the primary zone and column for substantially filling each of the latter with eluant, and collecting said supply of primary stage end products;

clearing said primary zone of eluant and collecting the latter for reuse;

passing a stream of said primary stage end products through a secondary concentration zone containing a second adsorption media, and adsorbing at least a portion of said end products on the second media;

thereafter passing a second eluant through the second media for desorbing at least a portion of the end products adsorbed thereon and producing a stream comprising secondary stage desorbed products and second eluant; and treating said secondary stage desorbed products to produce a supply of final products more concentrated than said supply of primary stage end products.

2. The method of claim 1 wherein said first and second adsorption media are activated carbon.

3. The method of claim 1 wherein said primary and secondary concentration zones are separate.

4. The method of claim 1 wherein said dilute stream contains quantities of acetic acid, methanol, furfural and sulfur dioxide.

5. The method of claim 1 wherein is included the step of purging said first and second adsorption media subsequent to the respective desorptions thereof.

6. The method of claim 5 wherein said first and second adsorption media are each purged with steam.

7. The method of claim 1 wherein said first and second eluants are respectively selected from the group consisting of the lower alcohols, acetone and moisture.

8. The method of claim 7 wherein said eluants are respectively selected from the group consisting of methanol, ethanol and steam.

9. The method of claim 1 wherein said concentrated supply of final products is a concentrated supply of said chemicals.

10. The method of claim 1 wherein said concentrated supply of final products is a concentrated supply of conversion products made during said method from said chemicals.

11. The method of claim 1 wherein is included the step of recovering said concentrated supply of final products.

12. The method of claim 1 wherein said primary stage desorbed products include the reaction products between said chemicals and said first eluant.

13. The method of claim 1 wherein said secondary stage desorbed products include the reaction products between the adsorbed primary stage end products and said second eluant.

14. The method of claim 1 wherein said primary stage end products and final products are, respectively, identical with said primary stage desorbed products and said secondary stage desorbed products.

15. The method of claim 1 including the step of recovering said second eluant derived as a result of the treatment of said secondary stage desorbed products.

16. The method of claim 1 wherein said supply of primary stage end products is in a carrier agent.

17. The method of claim 16 wherein said first eluant and carrier agent are different.

18. The method of claim 16 wherein said first eluant and carrier agent are moisture.

19. A method of concentrating a dilute supply of acetic acid to provide a concentrated supply of ethyl acetate, comprising the steps of:

directing said dilute supply of acetic acid to a primary concentration zone containing activated carbon;

adsorbing at least a fraction of said acetic acid onto said activated carbon;

desorbing said adsorbed acetic acid by contacting said primary zone activated carbon with methanol to produce a supply of methyl acetate more concentrated than said supply of dilute acetic acid;

treating said supply of methyl acetate in a first fractional distillation zone with sufficient moisture and under reaction conditions to reconvert the methyl acetate to acetic acid and to separate the latter to yield a primary stage supply of acetic acid more concentrated than said dilute supply;

directing said primary stage supply of acetic acid to a secondary concentration zone containing activated carbon;

adsorbing at least a fraction of the acetic acid directed to said second stage onto the activated carbon of the latter;

desorbing sad adsorbed acetic acid by contacting the secondary stage activated carbon with ethanol to thereby produce a supply of ethyl acetate;

concentrating said supply of ethyl acetate in a second fractional distillation column in order to produce a supply thereof more concentrated than said primary stage supply of acetic acid; and recovering said concentrated supply ethyl acetate.

20. The method of claim 19 wherein is included the steps of purging the activated carbon in each of said primary and secondary concentration zones with steam.

21. The method of claim 19 wherein said primary and secondary concentration zones each comprise elongated columns filled with activated carbon, and wherein the methanol employed in said first desorbing step, and the ethanol employed in said second desorbing step, is initially passed downwardly through the corresponding carbon column, and thereafter upwardly therethrough.

22. The method of claim 19 wherein the methanol employed in said first desorbing step, and the ethanol employed in said second desorbing step, are vaporized.

23. The method of claim 19 wherein said dilute supply of acetic acid contains quantities of acetic acid, methanol, furfural and sulfur dioxide.

24. A method of concentrating a dilute supply of acetic acid to provide a concentrated supply thereof, said method comprising the steps of:
directing said dilute supply of acetic acid to a primary concentration zone containing activated carbon;
adsorbing at least a fraction of said acetic acid onto said activated carbon;
desorbing said adsorbed acetic acid by contacting said primary zone activated carbon with methanol to produce a supply of methyl acetate;
treating said supply of methyl acetate in a first fractional distillation zone in the presence of sufficient moisture and under reaction conditions to reconvert the methyl acetate to acetic acid and to separate the latter to yield a primary stage supply of acetic acid more concentrated than said dilute supply;
directing said primary stage supply of acetic acid to a secondary concentration zone containing activated carbon;
adsorbing at least a fraction of the acetic acid directed to said secondary stage onto the activated carbon of the latter;
desorbing said adsorbed acetic acid by contacting the secondary stage activated carbon with an eluant to thereby remove said acetic acid and produce a supply of secondary stage desorbed products;
concentrating the supply of secondary stage desorbed products to produce a supply of concentrated secondary stage end products; and
recovering said supply of secondary stage end products.

25. The method of claim 24 wherein said eluant is steam and said secondary stage desorbed products include a supply of and acetic acid.

26. The method of claim 24 wherein said eluant is methanol and said secondary stage desorbed products include a supply of methyl acetate.

27. The method of claim 26 wherein is included the steps of:
treating said methyl acetate in a first fractional distillation zone in the presence of sufficient moisture and under reaction conditions to reconvert the methyl acetate to acetic acid and separate the latter; and
recovering the separated acetic acid as said primary stage supply thereof.

28. The method of claim 26 wherein is included the step of purging the activated carbon in said secondary zone with steam.

29. A method of concentrating a dilute supply of furfural to provide a concentrated supply thereof, comprising the steps of:
directing said dilute supply of furfural to a primary concentration zone containing activated carbon,
adsorbing at least a fraction of said furfural onto said activated carbon;
desorbing said adsorbed furfural by conacting said primary zone activated carbon with methanol to produce a first supply of furfural in methanol;
treating said supply of furfural in a first fractional distillation zone in order to substantially separate the desorbed supply of furfural from the methanol and produce a primary stage supply thereof more concentrated than said dilute supply;
directing said primary stage supply of furfural to a secondary concentration zone containing activated carbon;
adsorbing at least a fraction of the primary stage supply of furfural to a secondary concentration zone containing activated carbon;
adsorbing at least a fraction of the primary stage supply of furfural directed to said secondary stage onto the activated carbon of the latter;
desorbing the furfural adsorbed in said secondary concentration zone by contacting the activated carbon therewithin with methanol to produce a second supply of furfural in methanol;
concentrating said second supply of furfural in a second fractional distillation zone in order to produce a supply thereof more concentrated than said primary stage supply; and
recovering said supply of more concentrated furfural.

30. The method of claim 29 wherein is included the step of recovering the furfural supply from said second fractional distillation zone by withdrawing a cut of the overhead distillate boiling in the range of from about 208° to 210° F.

31. The method of claim 29 wherein is included the steps of recovering the furfural supply from said second fractional distillation zone by allowing the furfural content of said supply to separate into a separate layer, and recovering said layer.

32. The method of claim 29 wherein said dilute stream contains quantities of acetic acid, methanol, furfural and sulfur dioxide.

* * * * *